United States Patent [19]
Eberhardt et al.

[11] Patent Number: 5,406,857
[45] Date of Patent: Apr. 18, 1995

[54] METHOD AND APPARATUS FOR TESTING OF CIRCUMFERENTIALLY COMPLIANT BIOPROSTHETIC VALVE

[75] Inventors: Carol E. Eberhardt, Fullerton; Mark J. Capps, Orange; Luis Salazar, Rowland Heights, all of Calif.

[73] Assignee: Medtronic, Inc., Minneapolis, Minn.

[21] Appl. No.: 910,933

[22] Filed: Jul. 9, 1992

[51] Int. Cl.⁶ .......................................... G01M 19/00
[52] U.S. Cl. ................... 73/866.4; 73/865.6; 73/37
[58] Field of Search ............ 73/866.4, 865.6, 168, 73/4 R, 37, 865.9; 434/268

[56] References Cited

U.S. PATENT DOCUMENTS

| | | | |
|---|---|---|---|
| 2,924,894 | 2/1960 | Hellund | 73/866.4 X |
| 3,208,448 | 9/1965 | Woodward | 623/3 |
| 3,601,877 | 8/1971 | Goosen | 623/2 |
| 3,631,607 | 1/1972 | Koff et al. | 73/866.4 X |
| 4,682,491 | 7/1992 | Pickard | 73/37 |
| 4,974,461 | 12/1990 | Smith et al. | 73/865.6 |
| 5,052,934 | 10/1991 | Carey et al. | 434/268 |
| 5,139,515 | 8/1992 | Robicsek | 623/1 |
| 5,272,909 | 12/1993 | Nguyen et al. | 73/37 |

FOREIGN PATENT DOCUMENTS

| | | | |
|---|---|---|---|
| 2704444 | 8/1977 | Germany | 73/866.4 |
| 418833 | 8/1974 | U.S.S.R. | 434/268 |
| 1347090 | 10/1987 | U.S.S.R. | 434/268 |
| 1488869 | 6/1989 | U.S.S.R. | 434/268 |

OTHER PUBLICATIONS

Optimal Design of Aortic Leaflet Prosthesis, *Journal of the Engineering Mechanics Division*, By Dhanjoo N. Ghista, Helmut Reul, Gautam Ray, and K. B. Chandran, Feb. 1978, pp. 97–117.

Optimal Prosthetic Aortic Leaflet Valve: Design Parametric and Longevity Analyses: Development of the Avcothane-51 Leaflet Valve Based on the Optimum Design Analysis, *Journal of Biomechanics*, Oct. 5/6, 1977 pp. 313–324.

Measurement of Turbulence in Aortic Valve Prostheses: An Assessment by Laser Doppler Anemometer, *Proceedings of a Symposium at the 14th Annual Meeting of the Association for the Advancement of Medical Instrumentation*, P. C. Lu, A. M. Sallam, and N. H. C. Hwang, Las Vegas, Nev., May 21, 1979 pp. 91, 94, 95, 108.

(List continued on next page.)

*Primary Examiner*—Tom Noland
*Attorney, Agent, or Firm*—Terry L. Wiles; Harold L. Patton

[57] ABSTRACT

A fixture for testing a circumferentially compliant bioprosthetic valve. The fixture comprises a silicone rubber simulated aorta which approximates the geometry of a healthy human aorta and a cradle for the aorta. The compliance characteristics of the aorta can be selected by varying the proportions of ingredients in the silicone rubber, so that simulated aortas of different compliance but identical geometries can be provided. The compliant valve is disposed inside the aorta and held in place by suturing or the like. In one embodiment, the aorta and valve are supported by means of a cylindrical cradle, with the inflow and outflow ends of the aorta being folded over cylindrical rims on the respective inflow and outflow ends of the cradle. End caps are then fitted in place over the folded-over ends of the aorta, the end caps having holes therein to allow flow through the aorta and valve. The end caps are provided with O-rings on their outer surfaces, so that the assembled fixture can be inserted into a testing apparatus, with the aorta and valve held in place in the sealed flow loop of the apparatus. In another embodiment, adapter rings are provided for the inflow and outflow ends of the aorta, with the ends of the aorta being folded over cylindrical rims disposed around the inner circumference of each of the adapter rings. The adapter rings are also provided with O-rings, allowing the ends of the aorta to be received in a testing apparatus so that the aorta and valve are disposed along the sealed flow loop of the apparatus.

4 Claims, 12 Drawing Sheets

OTHER PUBLICATIONS

Normal Aortic Valve Function in Dogs, *The American Journal of Cardiology*, Mano Thubrikar, PhD, Robert Harry, MD, Stanton P. Nolan, MD, FACC, Oct. 1977, vol. 40, pp. 563–568.

The Dynamic Aortic Root, *Journal of Thorac Cardiovascular Surgery*, Richard J. Brewer, M. D., David Deck, PhD, Bienvenido Capati, MD, and Stanton P. Nolan, MD., Sep. 1976, 72(3); pp. 413–417.

Assessment of Aortic Pressure–Volume Relationships with an Impedance Catheter, *Catheterization and Cardiovascular Diagnosis*, 15:27–36 (1988), by Jmaes J. Ferguson, III, MD, Michael J. Miller, MD, Peter Sahagian, BA, Julian M. Aroesty, MD and Raymond G. McKay, MD.

The Geometry of the Aortic Root in Health at Valve Disease and After Valve Replacement, *Journal of Biomechanics*, by H. Reul, A. Vahlbruch, M. Giersiepen, Th. Schmitz-Rode, V. Hirtz and S. Effert. vol. 23, No. 2, pp. 181–191 (1990).

Aortic Distensibility Abnormalities in Coronary Artery Disease, *American Journal of Cardiology*, by Christodoulos Stefanadis, MD, Charles F. Wooley, MD, Charles A. Bush, MD, Albert J. Kolibash, MD and Harisios Boudoulas, MD., pp. 1300–1304, 1987.

METHOD AND APPARATUS FOR TESTING OF CIRCUMFERENTIALLY COMPLIANT BIOPROSTHETIC VALVE

FIELD OF THE INVENTION

This invention relates generally to the field of bioprosthetic devices, and more particularly to a method and apparatus for in vitro testing of bioprosthetic valves.

BACKGROUND OF THE INVENTION

In the field of bioprosthetic devices, a wide variety of different aortic valve prostheses have been shown in the prior art. Two main categories of valve prostheses can be defined: mechanical valves, including the so-called "caged ball", "caged disc", and "tilting disc" types; and tissue valves, which have leaflets. Of the various aortic valve prostheses currently known, the mechanical valves tend to be more circumferentially rigid than tissue valves. Tissue valves are typically stented and may be more or less circumferentially rigid, depending upon the rigidity of the stent.

It is believed by the inventors, however, that less rigid bioprosthetic valves, particularly ones of the tissue type, would be preferable in some cases since they more closely simulate a natural aortic valve and would therefore be less likely to create problems in the patient with unfavorable systolic and diastolic turbulence patterns, systolic pressure gradients, or embolic episodes. Further, it is believed that compliant bioprosthetic valves, having qualities more closely matched to natural aortic valves, would tend to have better flow efficiency, superior hydraulic characteristics, and flow patterns that are significantly less trauma-promoting and less likely to produce such undesirable effects as thrombus, atherosclerosis, or hemolysis.

While "leaflet" type bioprosthetic valves (of either the stented and non-stented variety) have been shown to more closely resemble a natural aortic valve in operation, experience has shown that fatigue-related failure of the leaflets can occur. This potential has heightened the need for rigorous stress analysis and testing of bioprosthetic valves. Typically, the development of a bioprosthetic valve involves several iterations of the following steps: (1) fabrication of prototypes in various sizes; (2) in vitro (fluid-mechanical, structural, and fatigue) testing of the prototypes; and (3) refinement and re-fabrication.

Of course, it is important for the conditions of any in vitro testing of bioprosthetic devices to simulate, as closely as possible, the in vivo conditions to which the tested devices will be exposed upon implant in patients. In the case of stented bioprosthetic valves, it is a simple matter to rigidly dispose a valve prosthesis, which is itself circumferentially rigid, along a fluid flow path for the purposes of testing. In conventional practice, a stented valve is fitted into a rigid valve holder and secured in place therein by means of a threaded retaining ring. The entire circumferentially rigid valve and valve holder can then be easily introduced into the flow path of various types of testing equipment.

It has been the inventors' experience, however, that in the case of a non-stented valve, it is substantially more difficult to provide a fixture for introducing the non-stented valve into a flow path during in vitro testing that, while providing support for the valve, does not interfere with the physiological functioning of the valve. In particular, it is believed to be desirable to provide a test fixture for non-stented bioprosthetic valves which does not restrict the circumferential compliance of the valve, so that the effects of the valve's compliant circumferential expansion and contraction of the valve can be observed and monitored during the in vitro testing.

In vitro evaluation of non-stented aortic bioprostheses requires that the valve be mounted in a test chamber that reasonably simulates the human aortic root. The use of a simulated or synthetic aortic root has been proposed in the prior art. Artificial aortic roots have been discussed, for example, in Reul et at., "Optimal Design of Aortic Leaflet Prosthesis", *American Society of Civil Engineers, Journal of the Engineering Mechanics Division*, v. 104, n. 1, Feb. 1978, pp. 91–117; in Ghista et al., "Optimal Prosthetic Aortic Leaflet Valve: Design Parametric and Longevity Analyses: Development of the Avcothane 51 Leaflet Valve Based on the Optimum Design Analysis", Journal of Biomechanics, 10/5–6, 1977 pp 313–324; and in Lu et al., "Measurement of Turbulence in Aortic Valve Prostheses: An Assessment by Laser Doppler Anemometer", *Proceedings of a Symposium at the 14th Annual Meeting of the Association for the Advancement of Medical Instrumentation*, Las Vegas, Nev., May 21, 1979, Yoganathan et al., editors. The foregoing Reul et al., Ghista et al., and Lu et al. references are incorporated herein by reference in their entirety.

In developing a simulated aorta for in vitro use, several factors must be considered. First, the aortic valve in its natural state does not have a fixed shape, and can only be described at a given time in the cardiac cycle, such as mid-systole or mid-diastole. Second, the human aorta is anisotropic and expands quite easily at low internal pressure but stiffens at higher pressures to prevent ballooning (this is discussed in Thubrikar et al., "Normal Aortic Valve Function in Dogs", *American Journal of Cardiology*, vol. 40, October 1977; in Brewer et al., "The Dynamic Aortic Root", *Journal of Cardiovascular Surgery*, Jun. 3, 1976; and in Ferguson et al., "Assessment of Aortic Pressure-Volume Relationships With an Impedance Catheter", *Catheterization and Cardiovascular Diagnosis*, 15:27–36, 1988). The foregoing Thubrickar et al., Brewer et al., and Ferguson et al. references incorporated herein by reference in their entirety.

Finally, since in vitro evaluation of an aortic bioprosthesis requires extended testing, a material which provides bacterial stability is necessary. Materials such as rubber provide bacterial stability and can be easily produced to exact geometric dimensions, but these materials are isotropic and do not exhibit the same locking characteristics at high pressures that are seen with anisotropic materials. For these reasons, it would be advantageous to provide a simulated aorta of repeatable geometric design and having controllable compliance characteristics to provide reasonable in vitro model aortas.

With the in vitro testing arrangement proposed by Lu et al. in the above-cited reference, the compliance factor for a flow loop system including a simulated aortic root is provided not by the simulated root itself, but rather by means of a compliance chamber disposed on the outflow side of the valve being tested. In the above-cited Reul et al. and Ghista et al. references, the artificial aortic root is made from polyurethane by a dipping process, so that the desired compliance is achieved by controlling the thickness of the polyurethane at the time the artificial aorta is fabricated. The Reul et al. flow loop additionally contains a compliance element for approximating natural compliance factors during testing.

There are numerous types of tests that must be performed on bioprosthetic aortic valves in order to evaluate their effectiveness and in order to obtain regulatory agency approval for public use of such devices. Among the more common of these tests are: steady flow studies, which focus on hydromechanical performance of the valves; pulsatile flow studies, which are concerned with valve dynamics (opening and closing times, leaflet motion, and the like), forward and backward (regurgitating) flow patterns, the pressure gradients across the valve, and energy loss across the valve; and fatigue studies, which are concerned with the ability of the valve to withstand millions of cycles without fatigue-related failure.

In the prior art, it has generally been the case that all of the necessary in vitro test data cannot be obtained from a single model setup, and that for each different analytical purpose, specially designed test apparatus is required. Depending upon the nature of the data to be obtained from a particular test setup, certain aspects of the in vivo environment may not be accounted for in the setup. For example, it has been suggested in the prior art (see, e.g., the above-cited Reul et al. reference) that for the purposes of steady flow tests, it is sufficient to dispose the valve being tested in a simple straight tube of constant diameter, rather than in a flow channel that simulates the subtle geometries of a human aorta. Likewise, for example, it may be deemed unnecessary during fatigue testing to simulate the circumferential compliance of the aortic root, whereas the compliance factor might be considered highly significant during pulsatile flow analysis.

Since several different test apparatuses may be required to obtain desired test data for a device, and since the different test apparatuses may be commercially-available from different vendors, it is often the case that the fixtures used to support the device being tested in a flow loop will differ from one test setup to the next. Depending upon the type of fixture used for a given setup, it may be difficult or impossible to utilize the same valve and/or simulated aortic root in more than one test. As a result, test data obtained from one test setup may not be accurately and meaningfully correlated with the data obtained from a different test. The inability to re-use a valve in a test setup may even limit the ability to obtain reproducible results even from the same test setup.

SUMMARY OF THE INVENTION

The present invention relates to a method and apparatus for the in vitro testing of bioprosthetic valves. The apparatus comprises a simulated aorta made of a material having controllable compliance characteristics. The bioprosthetic valve to be tested is affixed inside the simulated aorta. The aorta and valve are then disposed within a test fixture which supports the aorta at its ends only, so as not to interfere with the compliance of the simulated aorta in the area of the valve. The test fixture is adapted to be made an integral part of the sealed flow loop of one or more than one testing apparatus, so that the operation of the bioprosthetic valve can be tested in a manner which takes into account the effects of the valve's compliance.

BRIEF DESCRIPTION OF THE DRAWINGS

With the considerations such as are set forth in the foregoing discussion, the inventors will describe herein a method and apparatus for in vitro testing of circumferentially compliant bioprosthetic devices. Various aspects of the present invention will be best understood with reference to the following detailed description of specific embodiments of the invention, when read in conjunction with the accompanying drawings, wherein.

DETAILED DESCRIPTION OF A SPECIFIC EMBODIMENT OF THE INVENTION

Figure 1A:
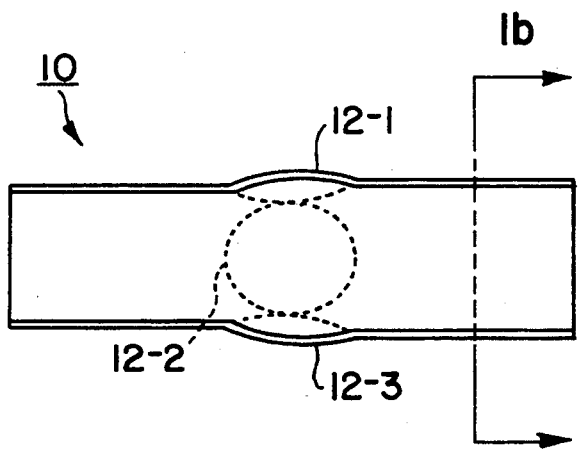
FIG. 1a and 1b are side and end views, respectively, of a simulated aorta in accordance with one embodiment of the present invention.
Figure 1B:
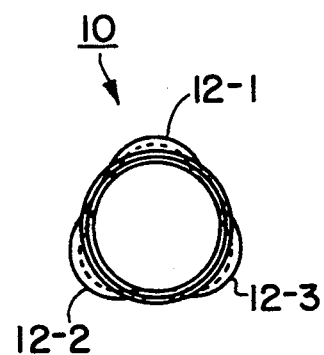

Referring to FIGS 1a and 1b, there are shown side and end views, respectively, of a simulated aorta 10 in accordance with one embodiment of the present invention. In keeping with one aspect of the present invention, aorta 10 of FIGS. 1a and 1b is provided with three sinuses, 12-1, 12-2, and 12-3, which imitate the natural anatomy of a human aorta. Aorta 10 is, in the presently disclosed embodiment of the invention, approximately 10-cm long, and can be formed in various diameters, typically ranging between 15-mm or so to 30-mm or so.

Simulated aorta 10 has been patterned from dimensional data available through published clinical literature. The geometry of aorta 10 is based upon the normal human adult aorta, as reported, for example, by Reul et al., in "The Geometry of the Aortic Root in Health, at Valve Disease, and After Valve Replacement", *Journal of Biomechanics*, v. 23, n. 2, 1990, which article is hereby incorporated by reference in its entirety. A normal aorta was used rather than a diseased one, since the geometry of the diseased aorta varies as a result of the type and extent of the disease, as reported by Reul et al. and by Stefandadis, et al., "Aortic Distensibility Abnormalities in Coronary Artery Disease", *American Journal of Cardiology*, 59: 1300-1304, 1987, which article is hereby incorporated by reference in its entirety. By using a normal aorta as a model, a more normal distribution of the shape is reflected (see Reul et al.).

It should be noted from FIGS. 1a and 1c that one end of aorta 10, hereinafter referred to as the "inflow end", has a slightly smaller diameter than the other end, hereinafter referred to as the "outflow end".

In order that simulated aorta 10 can be reproduced with consistent and repeatable geometry and dimensions, a steel compression mold was produced. In accordance with one feature of the present invention, aorta 10 is preferably made of silicone rubber. As would be appreciated by those of ordinary skill in the materials sciences, the silicone rubber can be variously formulated such that for a given thickness, a range of compliancies can be achieved. In particular, it has been found by the inventors that by carefully controlling the proportions of ingredients in the silicone rubber, the compliance of a simulated aorta made therefrom can be precisely selected with a high degree of precision and consistency. This is significant since with the techniques of the prior art known to the inventors, compliancy has been controlled either through the use of a separate compliancy chamber disposed along the test setup flow loop, or by varying the thickness of the simulated aorta. Having to vary the thickness of the aorta is deemed to be undesirable since the geometry of the test aorta is thus not held constant over successive trials of a given test at different compliancies. In the presently disclosed embodiment of the invention, aorta 10 is preferably molded using silicon rubber and cured for 24 hours to stabilize the material.

Results from the inventors' simulated aorta characterization studies show that simulated aortas such as aorta 10 in accordance with the presently disclosed embodiment of the invention, compression molded using a specific Durometer silicone rubber, provided a consistent compliance for each of various sizes of aorta. In particular, the aortas demonstrated a compliance quantified as a 4% ±1.0% diameter change per 40-mmHg pressure change, and remained within these limits over a pressure range of 40 to 200-mmHg.

Figure 1C:
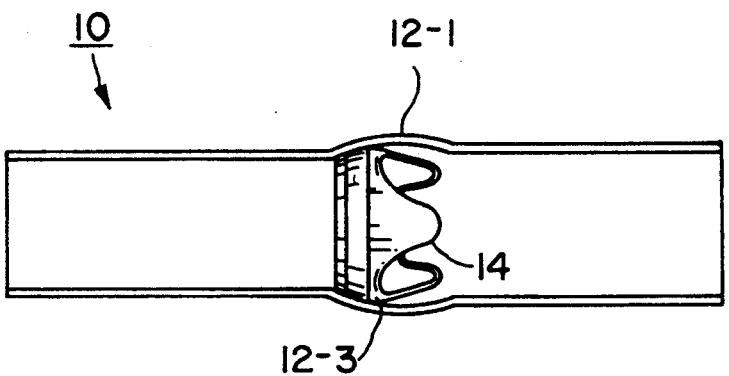
FIG. 1c is a side view of the aorta from FIGS. 1a and 1b showing a bioprosthetic valve disposed therein.

In FIG. 1c, simulated aorta 10 is shown having a bioprosthetic valve 14 disposed therein. Valve 14 is mounted in simulated aorta 10 by suturing the valve base and commissure tips, in accordance with known techniques in the art. Suture holes are preferably filled with ordinary liquified silicone rubber which is allowed to cure prior to testing, in order to prevent leakage of the aorta when it is disposed in a sealed test flow loop. As can be appreciated by those of ordinary skill in the art, the configuration shown in FIG. 1c provides minimal support for valve 14, and allows circumferential compliance during testing. Simulated aorta 10 does not interfere with the physiological functioning of the valve.

Although a particular type of valve 14 is depicted inside simulated aorta 10 in FIG. 1c, it is to be understood that this is done for the purposes of illustration only. Many different types of valves, whether they are mechanical or tissue valves, stented or non-stented, circumferentially rigid or circumferentially compliant, may be effectively tested using the method and apparatus of the present invention.

Figure 2:
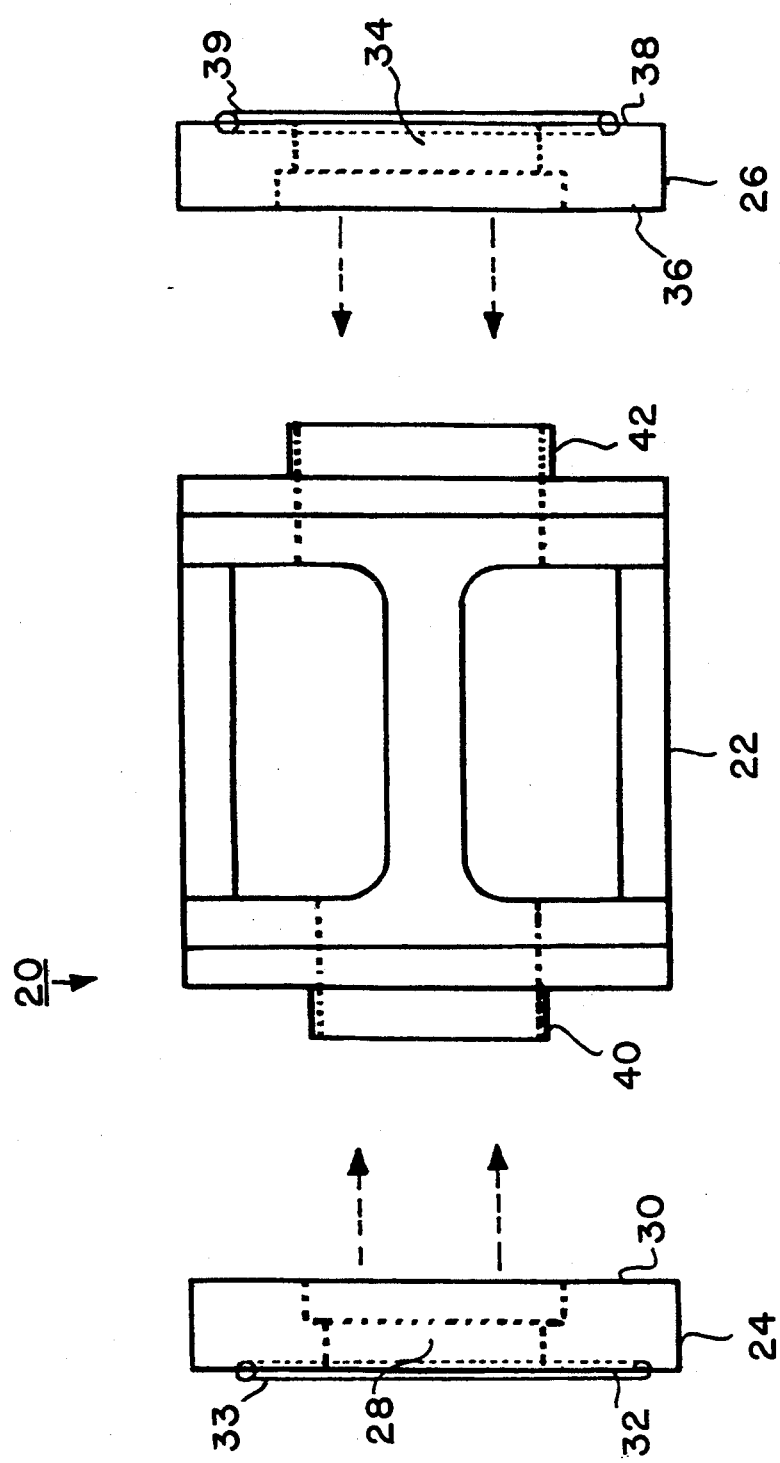
FIG. 2 is an exploded side view of a test fixture in accordance with one embodiment of the present invention.
Figure 3:
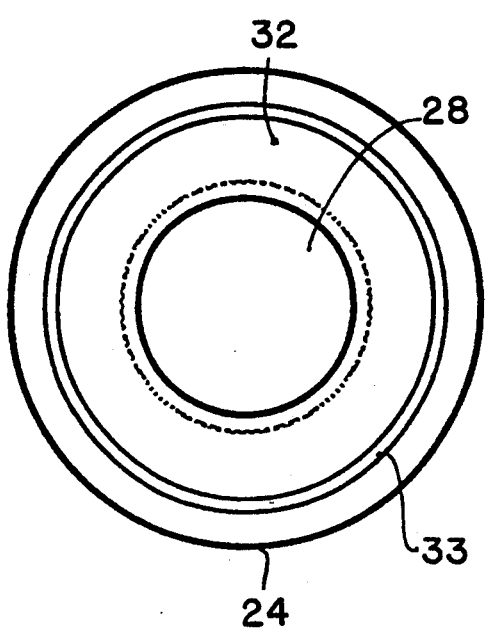
FIG. 3 is an end view of an end cap from the fixture of FIG. 2.
Figure 4:
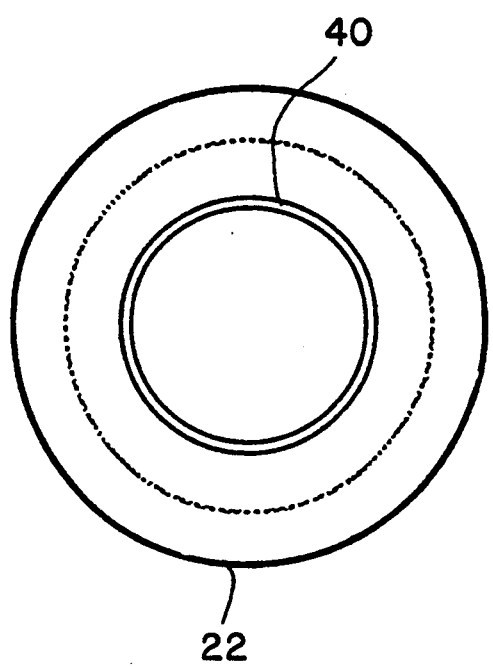
FIG. 4 is an end view of a central cradle portion of the fixture of FIG. 2.

Turning now to FIG. 2, an exploded view of a fixture 20 for supporting aorta 10 in accordance with one embodiment of the present invention is shown. Fixture 20 of FIG. 2 comprises three parts: a substantially cylindrical cradle portion 22, a substantially circular inflow end cap 24, and a substantially circular outflow end cap 26. An end view of inflow end cap 24 is shown in FIG. 3, and an end view of cradle 22 is shown in FIG. 4. Inflow end cap 24 and outflow end cap 26 are adapted to be fitted onto the inflow end and outflow end, respectively, of cradle 22, as will be hereinafter shown with reference to later figures. In particular, inflow end cap 24 has a circular opening 28 therethrough, with circular opening 28 having a slightly enlarged diameter on inner face 30 as compared to the diameter of opening 28 on the outer face 32 of cap 24. Similarly, outflow end cap 26 has a circular opening 34 therethrough, where opening 34 has a slightly larger diameter on the inner face 36 of cap 26 than on the outer face 38 of cap 26.

With continued reference to FIGS. 2 and 3, a rubber O-ring 33 is inset in the outer face 32 of inflow end cap 24. A similar O-ring 39 is inset in the outer face 38 of outflow end cap 26. As will become hereinafter apparent with reference to later figures, O-rings 33 and 39 enable fixture 20, once assembled in the manner to be hereinafter described, to be fitted into the flow loop of various test equipment such that the flow loop remains sealed.

Cradle 22 is provided with a cylindrical rim 40 on its inflow end, where the diameter of rim 40 is slightly smaller than the enlarged inner diameter of hole 28 in inflow end cap 24. Likewise, a cylindrical rim 42 disposed on the outflow end of cradle 22 has a diameter slightly smaller than the enlarged inner diameter of hole 34 in outflow end cap 26.

It should also be noted from FIG. 2 that the diameter of cylindrical rim 42 is somewhat larger than the diameter of cylindrical rim 40, and that the enlarged inner diameter of hole 34 in outflow end cap 26 is somewhat larger than the enlarged inner diameter of hole 28 in inflow end cap 24. The size differential between rim 42 and rim 40, and the corresponding size differential of holes 34 and 28 in respective end caps 26 and 24 is necessary due to the similar size differential between the outflow and inflow ends of simulated aorta 10, as previously noted with reference to FIGS. 1a and 1c.

Figure 5:
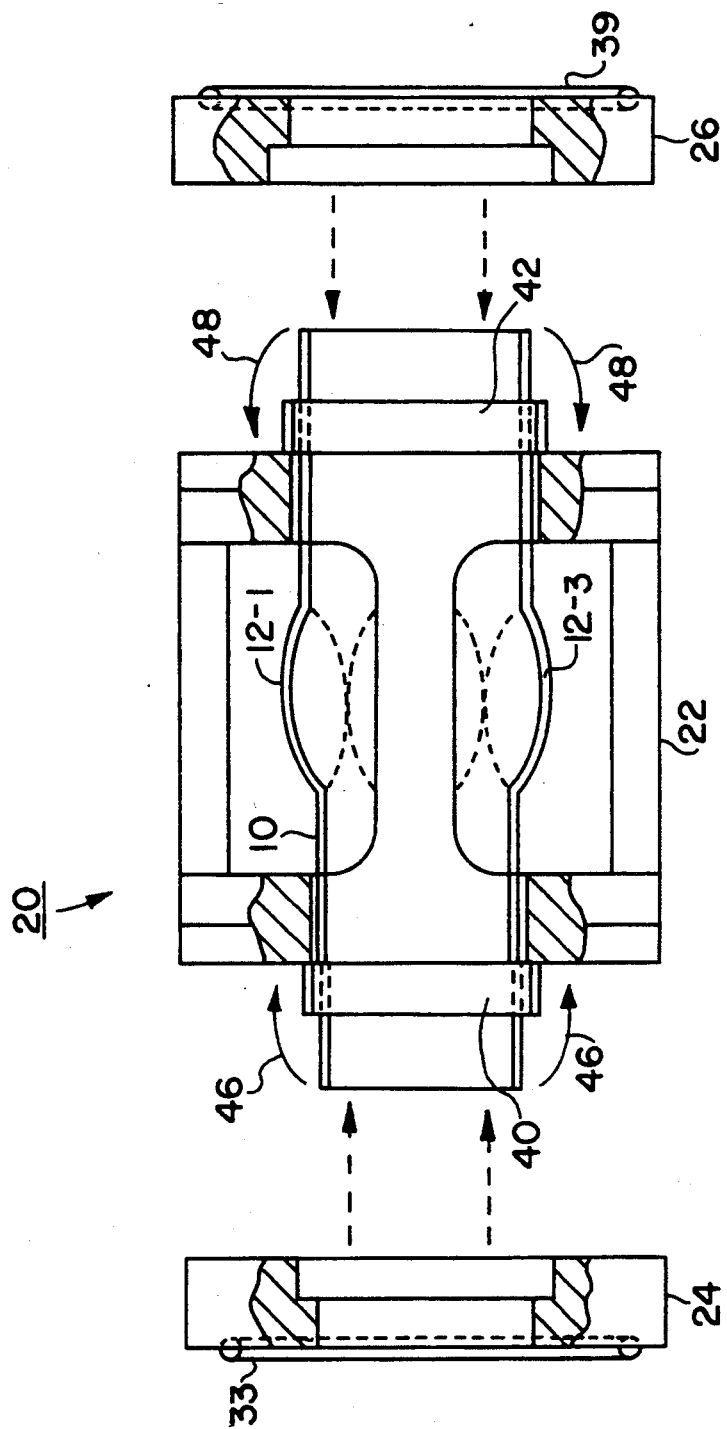
FIG. 5 is a partially cut-away exploded side view of the fixture of FIG. 2 having the aorta of FIGS. 1a, 1b, and 1c disposed therein.

With reference now to FIG. 5, a partially cut-away, exploded view of fixture 20 is shown, with aorta 10 from FIGS. 1a, 1b, and 1c having been inserted axially through the center of cradle 22. It is to be understood that prior to the insertion of simulated aorta 10 into cradle 22, a bioprosthetic valve, not shown in FIG. 5, is affixed inside simulated aorta 10, generally in the area of sinuses 12-1, 12-2, and 12-3, as previously described with reference to FIG. 1c. Once simulated aorta 10 has been inserted into cradle 22, the next stage in the process of assembling fixture 20 is to fold the inflow end of simulated aorta 10 back over cylindrical rim 40, in the direction indicated by arrows 46. Next, the outflow end of simulated aorta 10 is similarly folded back over cylindrical rim 42, in the direction indicated by arrows 48 in FIG. 5.

Figure 6:
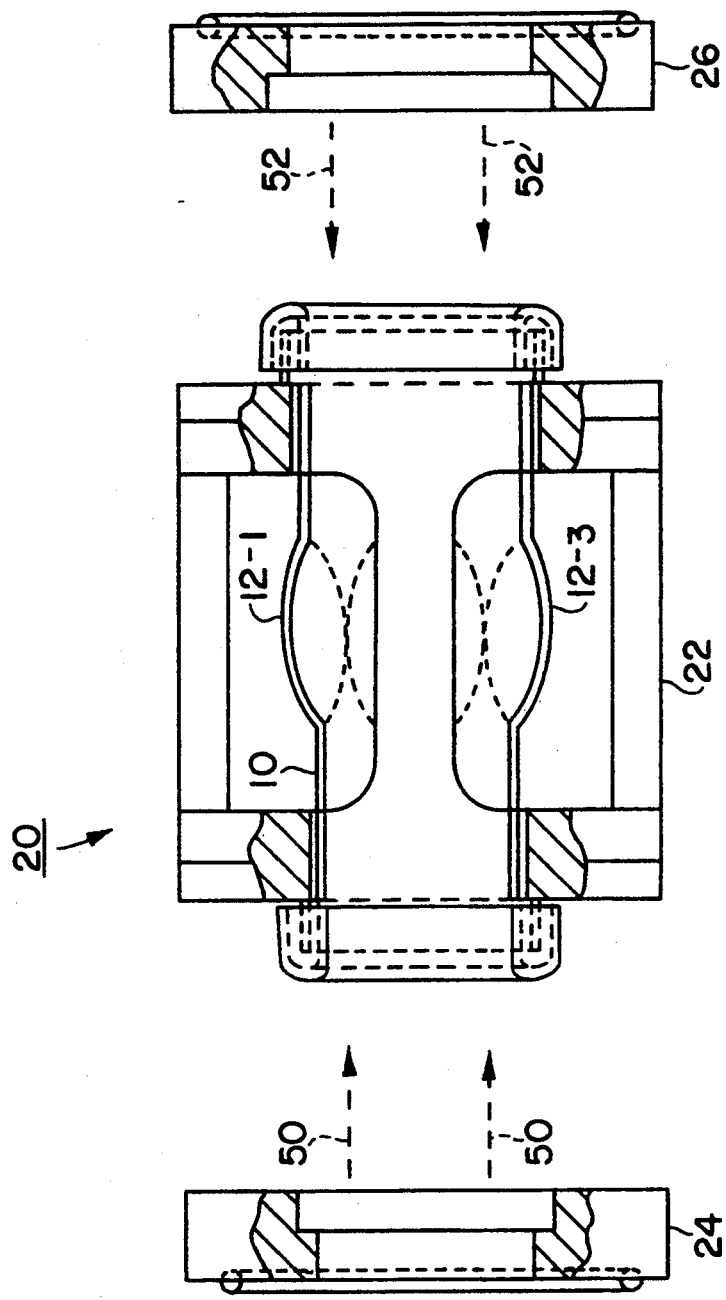
FIG. 6 is a partially cut-away exploded side view of the fixture and aorta from FIG. 5, wherein the aorta has been folded over a portion of the fixture.
Figure 7:
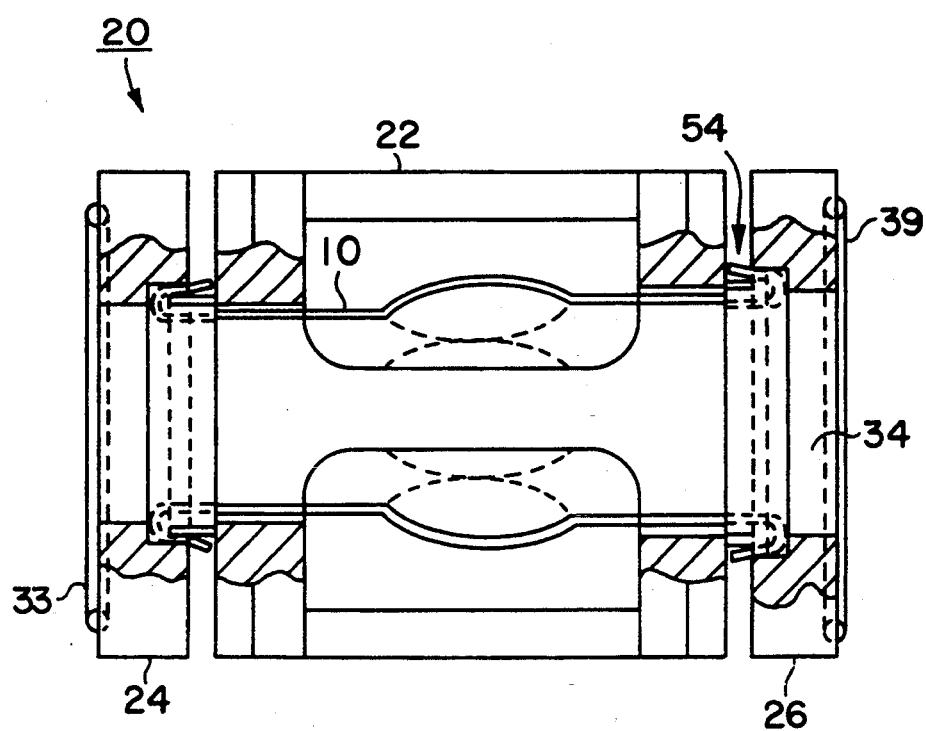
FIG. 7 is a partially cut-away side view of the fixture and aorta from FIGS. 5 and 6, fully assembled.
Figure 8:
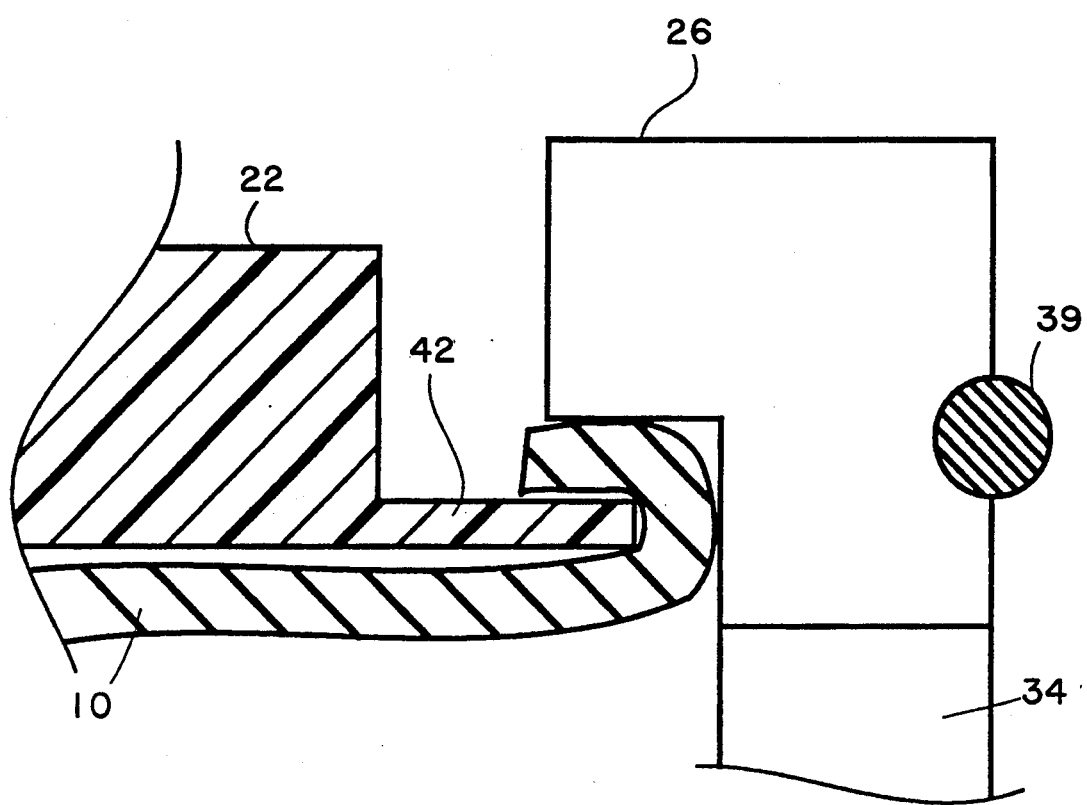
FIG. 8 is a greatly enlarged cross-sectional view of a portion of the fixture and aorta from FIG. 7.

Fixture 20 and simulated aorta 10, after the respective ends of aorta 10 are folded over rims 40 and 42, are depicted in FIG. 6. The next stage in the process of assembling fixture 20 and simulated aorta 10 is to fit end caps 24 and 26 onto the respective ends of cradle 22. In particular, inflow end cap 24 is pushed onto the inflow end of cradle 22, in the direction indicated by arrows 50 in FIG. 6. Fixture 20 and simulated aorta 10, after the respective end caps 24 and 26 have been fitted onto cradle 22, are depicted in FIG. 7. As can be seen from FIG. 7, the slightly larger inner diameter of respective holes 28 and 34 in caps 24 and 26 permits caps 24 and 26 to fit over the folded-over ends of simulated aorta 10, compressing the folded-over ends of simulated aorta 10 against rims 40 and 42 on cradle 22. A greatly enlarged view of the area denoted generally as 54 in FIG. 7 is shown in FIG. 8.

Figure 9:
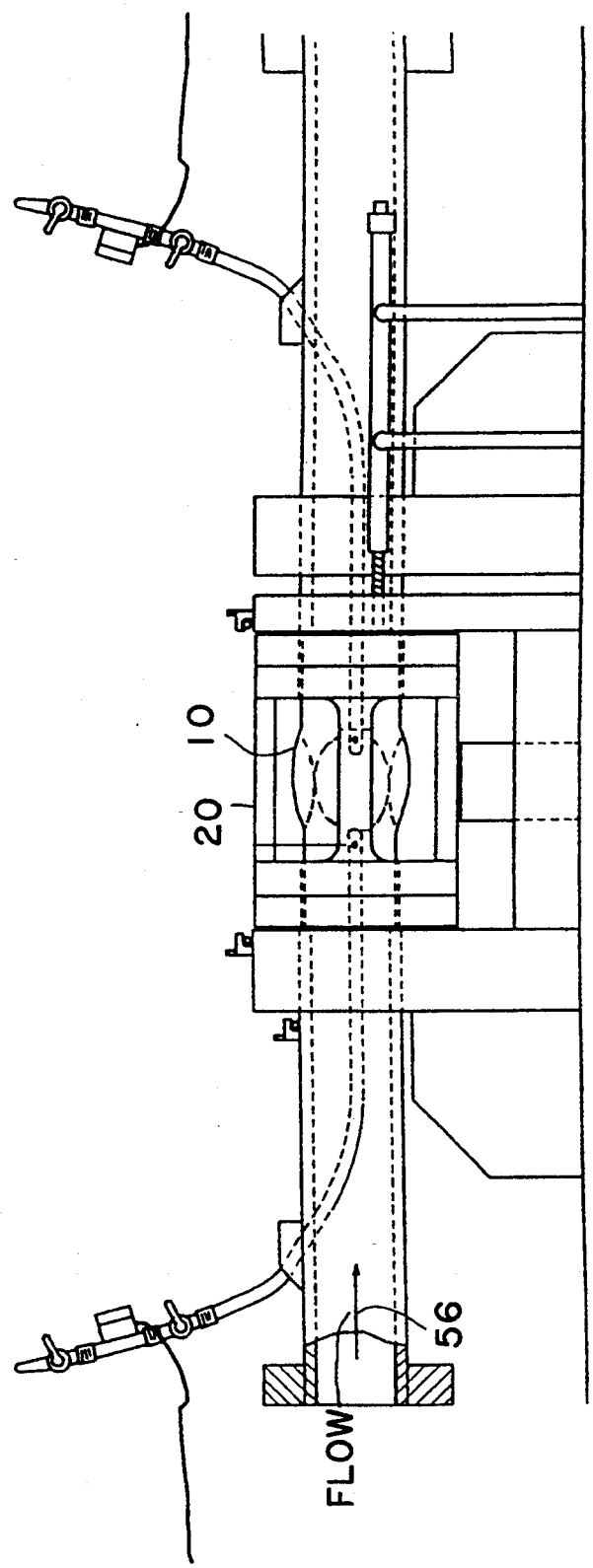
FIG. 9 is a side view of a test apparatus containing the aorta and fixture of FIG. 7.

Once assembled as shown in FIG. 7, fixture 20 provides support for aorta 10 and the bioprosthetic valve therein, without affecting the compliance of simulated aorta 10 in the area of sinuses 12-1, 12-2, and 12-3. By way of illustration, there is shown in FIG. 9 the assembled fixture 20 and simulated aorta 10 having been inserted into the flow loop of a pulsatile flow study apparatus, through which fluid flow is established in the direction indicated by arrow 56. In accordance with one aspect of the present invention, and as would be appreciated by those of ordinary skill in the art, fixture 20 and aorta 10 can be inserted and removed from various flow-loop apparatuses such as that shown in FIG. 9 without damage to aorta 10 and the bioprosthetic valve therein. In this way, the same simulated aorta/bioprosthetic valve combination can be subjected to a succession of different tests involving different flow loop apparatuses. Since the same aorta/valve combination can be used, the results from each one of the individual tests can be meaningfully and accurately correlated with the results from others in the succession of tests. As previously noted, this would not be possible if a different aorta/valve combination were used for each one of the tests.

Figure 10:
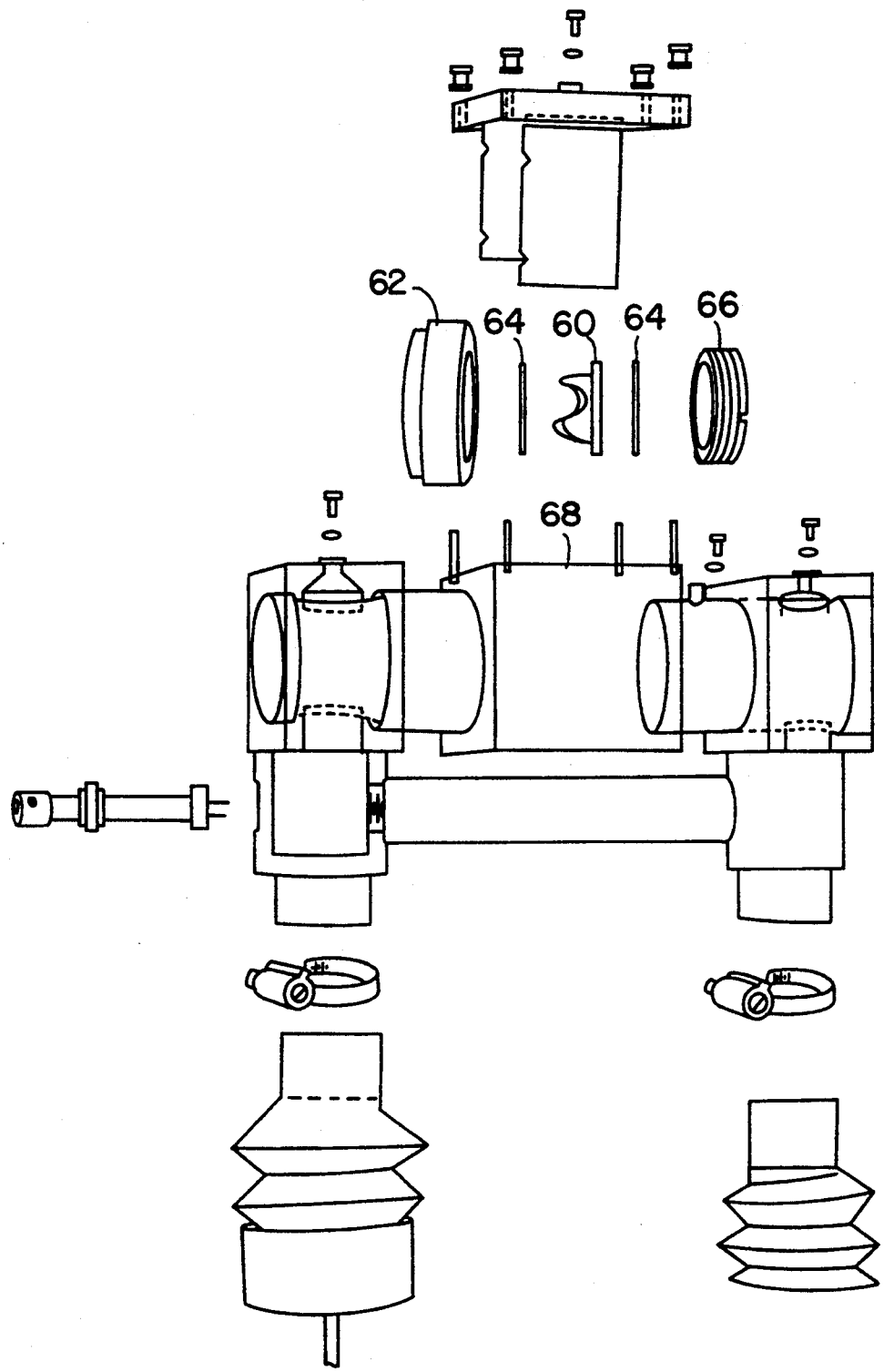
FIG. 10 is an exploded front view of a Shelhigh fatigue tester test chamber assembly of the prior art.

Turning now to FIG. 10, an exploded view of a test chamber assembly from a commercially-available Shelhigh 300 TM Fatigue Test System is shown. The configuration shown in FIG. 10 is a conventional one, commonly utilized in the prior art for the purposes of fatigue testing of a stented (i.e., circumferentially rigid) bioprosthetic valve. In particular, a stented valve 60 is shown in FIG. 10. In accordance with the manufacturer's instructions, stented valve 60 is supported in the Shelhigh tester by means of a rigid valve holder 62. Retaining rings 64 are positioned on the inflow and outflow sides of valve 60, and retaining tings 64 and valve 60 are secured in valve holder 62 by a threaded ring 66. Valve holder 62 with valve 60 secured therein is then received in a test chamber 68, which holds valve holder 62 in the flow loop of the tester.

It is believed that other components of the Shelhigh test chamber assembly depicted in FIG. 10 would be familiar to those of ordinary skill in the art, and that such other components are not relevant to the present description of a particular embodiment of the invention. Accordingly, certain components of the test chamber assembly depicted in FIG. 10 will not be described herein in detail.

As would be further appreciated by those of ordinary skill in the art, the fatigue testing arrangement depicted in FIG. 10 is not entirely suitable for the purposes of testing non-stented or otherwise circumferentially complaint valves, since the rigidity of valve holder 62 would prevent circumferential expansion or contraction of the valve being tested, and would therefore prevent the investigator from obtaining reliable data concerning operation of the valve being tested.

In accordance with another feature of the presently disclosed embodiment of the invention, therefore, there is provided an adaptation of the test chamber assembly of FIG. 10 that allows a non-stented, circumferentially compliant valve to be supported in the flow loop of the Shelhigh tester in a manner that allows for the effects of the valves circumferential compliance to be accounted for in the course of the fatigue testing. In particular, and as shown in FIG. 11, the adaptation of the Shelhigh tester to accommodate compliant valves involves simulated aorta 10 previously described in detail with reference to FIGS. 1a, 1b, and 1c.

Figure 11:
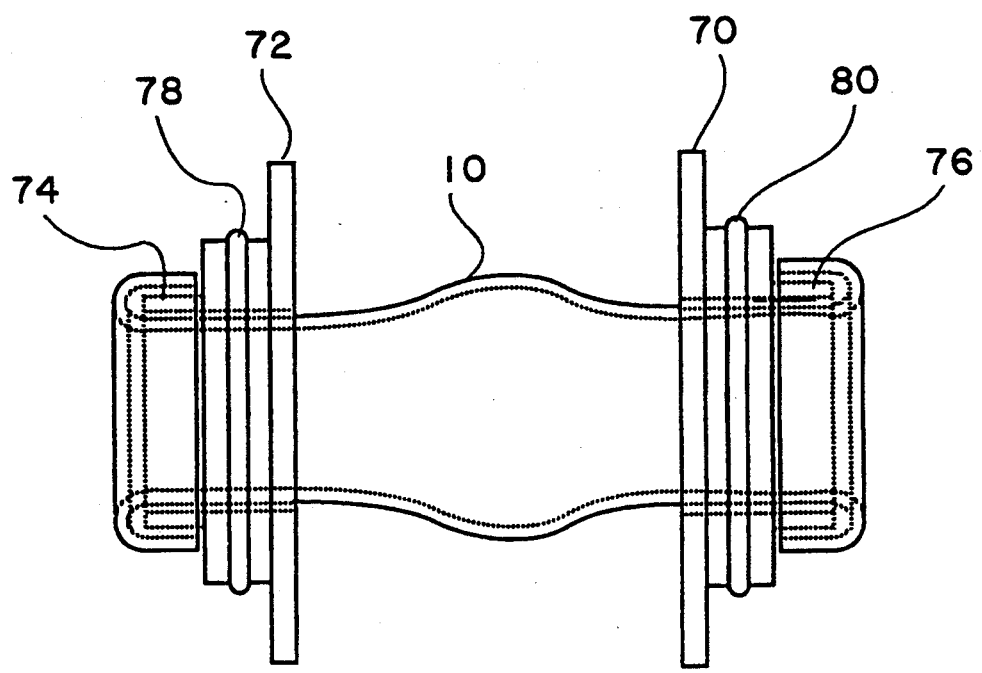
FIG. 11 is a side view of the aorta of FIGS. 1a, 1b, and 1c having adapter rings in accordance with one embodiment of the present invention attached thereto.

Simulated aorta 10 in FIG. 11 is introduced into the flow loop of the Shelhigh tester by means of an adapter ring 70 on the inflow side of aorta 10 and an adapter ring 72 on the outflow side of aorta 10. In accordance with the presently disclosed embodiment of the invention, adapter rings 70 and 72 are preferably capable of being received in test chamber 68 in place of the prior art valve holder assembly, including valve holder 62, retaining rings 64, and threaded ring 66.

Figure 12A:
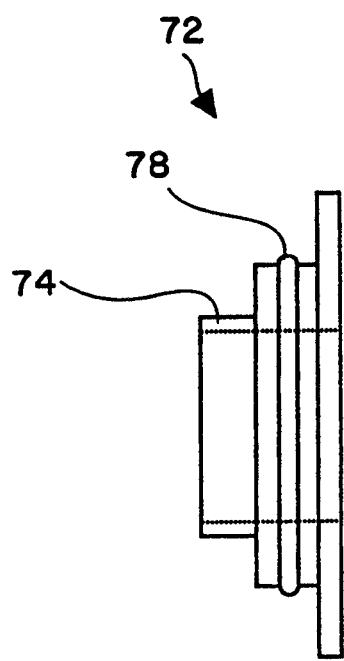
FIGS. 12a and 12b are side and end views, respectively, of one of the adapter rings from FIG. 11.
Figure 12B:
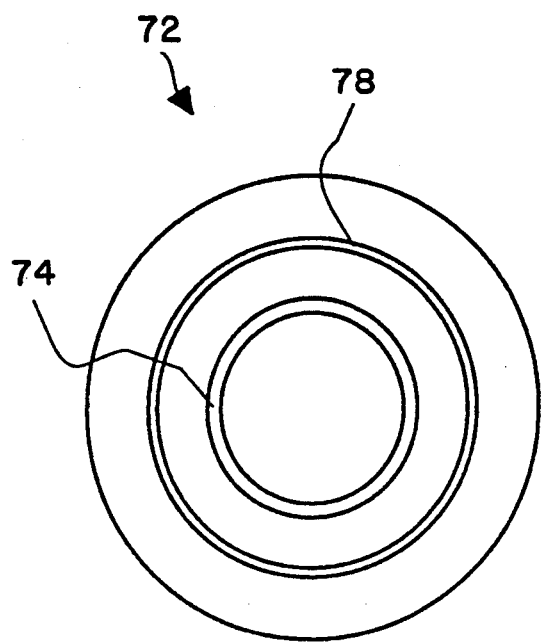

A side view of adapter ring 72 is shown in FIG. 12a, and an end view of adapter ring 72 is shown in FIG. 12b. Adapter ring 72 is provided with a cylindrical rim 74 that functions in much the same manner as cylindrical rims 40 and 42 in the embodiment of the present invention previously described with reference to FIG. 5. Of course, adapter ring 70 is similarly provided with a cylindrical rim, designated as 76 in FIG. 11. Adapter rings 72 and 70 are further provided with O-rings 78 and 80, respectively, which function to establish a seal between adapter rings 72 and 70 and test chamber 68 of the Shelhigh tester.

Figure 13:
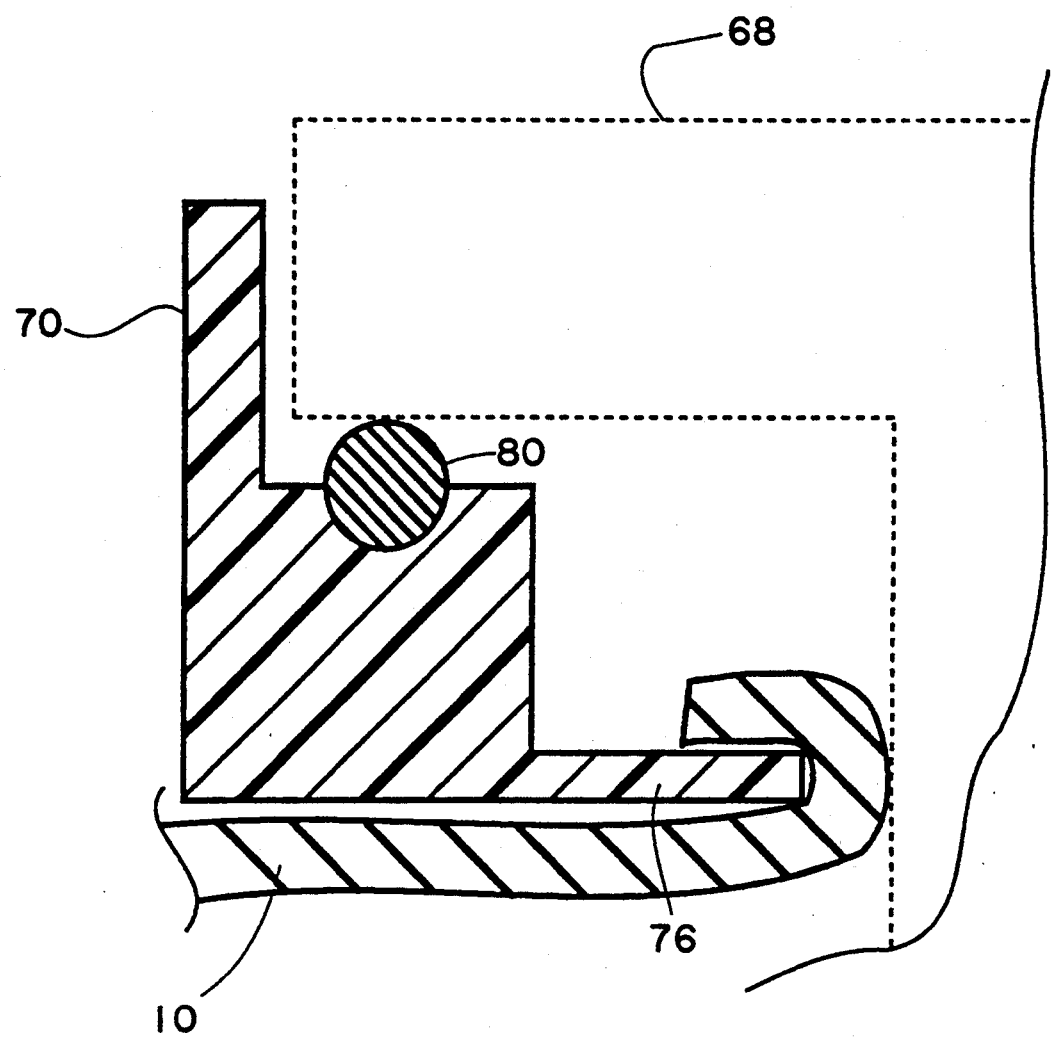
FIG. 13 is a greatly enlarged cross sectional view of part of the aorta and adapter ring from FIG. 11.

A greatly enlarged cross-sectional view of a portion of adapter ring 70 is provided in FIG. 13. The inflow end of simulated aorta 10 is folded around cylindrical rim 76 in the same manner as the ends of aorta 10 were folded around cylindrical rims 40 and 42 in the embodiment of the invention previously described with reference to FIG. 5. O-ring 80 forms a seal between adapter ring 70 and the inflow side of test chamber 68, which is shown in phantom in FIG. 13. It is to be understood of course that simulated aorta 10 is similarly coupled to adapter ring 72 on the outflow side of test chamber 68.

From the foregoing detailed description of specific embodiments of the present invention, it should be apparent that a fixture for facilitating the in vitro testing of bioprosthetic valves has been disclosed. Although particular embodiments of the invention have been described herein in some detail, this has been done for the purposes of illustration only, and is not intended to be limiting with respect to the scope of the invention as defined in the appended claims which follow. It has been contemplated by the inventors that various changes, alterations, or modifications may be made to the invention as described herein without departing from the spirit and scope of the invention as defined in the claims.

What is claimed is:

1. A fixture for in vitro testing of a circumferentially compliant bioprosthetic valve comprising:

a simulated aorta patterned from dimensions of a natural human aorta, having a generally hollow cylindrical shape with open inflow and outflow ends, said aorta having a predetermined circumferential compliance, and said aorta adapted to receive said circumferentially compliant bioprosthetic valve therein;

an inflow end adapter ring, generally annular in shape, having a cylindrical rim disposed around its inner circumference such that said inflow end of said aorta is received and supported to permit flow simulating natural blood flow through said aorta and valve, wherein the inflow end of said aorta is folded back over said cylindrical rim on said inflow end adapter ring; and an outflow adapter ring, generally annular in shape, having a cylindrical rim disposed around its inner circumference such that said outflow end of said aorta is received and supported to permit flow simulating natural blood flow through said aorta and valve, wherein the outflow end of said aorta is folded back over said cylindrical rim on said outflow end adapter ring; said inflow and outflow end adapter rings having fluid seals disposed thereon, allowing said rings to be received in respectively conforming receptacles in a testing apparatus, such that said aorta is disposed along a sealed test flow loop of said apparatus.

2. A method of testing a circumferentially compliant bioprosthetic valve, comprising the steps of:

(a) affixing said valve in a desired spatial relationship inside a simulated aorta having a predetermined circumferential compliance;

(b) inserting said aorta into a test fixture supporting opposing ends of said simulated aorta to permit flow simulating natural blood flow therethrough and to prevent interference with the compliance characteristics of said simulated aorta and said valve, said fixture comprising a support cradle and two circular rims to support the ends of said simulated aorta in a folded over relationship;

(c) providing said test fixture with a fluid seal at each of said opposing ends to permit said aorta and said valve to be disposed along a sealed flow loop of said testing apparatus.

3. A method in accordance with claim 2, further comprising the steps of:

(d) installing said test fixture into a series of test apparatuses without disrupting said spatial relationship of said aorta and said valve.

4. A method in accordance with claim 2, where said valve is non-stented.

* * * * *